United States Patent
Wyatt et al.

(10) Patent No.: US 6,774,994 B1
(45) Date of Patent: Aug. 10, 2004

(54) METHOD AND APPARATUS FOR DETERMINING ABSOLUTE NUMBER DENSITIES OF PARTICLES IN SUSPENSION

(75) Inventors: Philip J. Wyatt, Santa Barbara, CA (US); Miles J. Weida, Santa Barbara, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 0 days.

(21) Appl. No.: 10/640,893

(22) Filed: Aug. 13, 2003

(51) Int. Cl.[7] .............................................. G01N 21/00
(52) U.S. Cl. ...................... 356/337; 356/336; 356/340; 356/341; 356/343
(58) Field of Search ................................ 356/335–343, 356/72–73, 435, 441; 250/574–575

(56) References Cited

U.S. PATENT DOCUMENTS

| | | | | |
|---|---|---|---|---|
| 4,541,719 A | * | 9/1985 | Wyatt ........................ | 356/343 |
| 4,616,927 A | * | 10/1986 | Phillips et al. .............. | 356/338 |
| 5,129,723 A | * | 7/1992 | Howie et al. ................ | 356/336 |
| 5,305,071 A | * | 4/1994 | Wyatt ......................... | 356/73 |
| 6,219,138 B1 | * | 4/2001 | Swanson et al. ............ | 356/336 |

* cited by examiner

Primary Examiner—Frank G. Font
Assistant Examiner—Sang H. Nguyen
(74) Attorney, Agent, or Firm—Philip J. Wyatt (57) ABSTRACT

A method for determining absolute number densities of particles in a solution is disclosed based on a light scattering method. A light scattering photometer is calibrated to produce the Rayleigh ratio at each angle measured with respect to light scattered per unit incident intensity, per unit volume illuminated within the field of view of each detector per steradian subtended by said detector. In order that the numbers calculated be accurate, the illuminated particles should be effectively monodisperse. From the excess Rayleigh ratios measured at a plurality of angles with respect to the incident light beam illuminating said sample particles, an effective size is calculated which, in turn, is used to calculate the differential scattered intensity at each angle. The number of particles per unit volume element is then determined from the measured excess Rayleigh ratio divided by the corresponding differential scattered intensity.

29 Claims, 5 Drawing Sheets

METHOD AND APPARATUS FOR DETERMINING ABSOLUTE NUMBER DENSITIES OF PARTICLES IN SUSPENSION

BACKGROUND

The determination of absolute particle numbers in a liquid suspension is a critical requirement for many types of particle-based applications. In the field of pharmaceuticals, particles such as liposomes, microcapsules, viruses, and emulsions, for example, are used often for the delivery of incorporated drugs or reagents. Therapeutic benefits of such particle drug therapy depend critically upon an a priori knowledge of the amount of drug being delivered and this, in turn, requires an accurate measure of the particle numbers per unit volume delivered to the patient.

For the case of virus carriers, such as the genetically-engineered parvovirus capsids and viruses designed to introduce a heterologous gene into a target cell described by Rabinowitz et al. in their U.S. Pat. No. 6,491,907, particle number is required to determine quantitatively the amount of heterologous genes transferred. Various techniques are discussed by the inventors to obtain accurate particle numbers. In their U.S. Pat. No. 6,447,995, Carrion, et al. use the characteristic fluorescence emission of the adenovirus techniques to estimate its number density. The importance of measurement of recombinant adeno-associated virus (rAAV) virion number is discussed further by Bankiewicz, et al. in their U.S. Pat. No. 6,309,634. Hutchins, et al. in their U.S. Pat. No. 6,248,514 state that ". . . Total particle measurement can be made by such techniques as electron microscopy of viral preparations or measurement of total DNA by optical density at 260 nm of a sodium dodecyl sulfate (SDS) treated virus suspension . . . " These techniques are labor intensive, time consuming, and still remain of questionable precision.

The quality and performance of toners used in xerography processes depend critically upon the number distribution present, i.e. the number density of particles of different sizes, as discussed, for example by Kuroda, et al. in their U.S. Pat. No. 6,395,443.

A variety of microparticles, especially polystyrene latex spheres, are used by the semiconductor manufacturers to calibrate their wafer inspection systems. Such systems include Quick Check Latex Sphere Calibration Standards for Tencor, KLA Surfscan, Estek, ADE, Aeronca and others. For these calibration tests it is important to characterize well the samples to be attached to the wafers. Not only should the particle sizes and size distributions be well established, but the absolute number of such particles per ml of solution used in the depositing equipment should be known as well.

Unfortunately, the determination of absolute particle number and distribution has been a difficult and time consuming task. The need for a rapid means to determine such quantities has long been recognized, even if such determinations were of moderately low precision. The present invention provides a means and method to achieve such results.

For the simplest case of monodisperse homogeneous spherical particles, it is the purpose of the invention to provide a means for providing an accurate measure of the particles' size and number density. Another objective of the invention is to provide means by which particles of generally spherical structure may be characterized similarly.

For the case of particle samples that may not be monodisperse, it is another objective of this invention to provide means by which, following their initial fractionation into size groups, they may be quantitated in terms of their absolute number density distributions.

For particles that are not of generally spherical shape, it is a further objective of this invention to provide guidance by which reasonable estimates of absolute particle number densities may be achieved.

For all its applications and objectives, this invention is specifically intended for particles in liquid suspension and within a size range of 10 to 1000 nm. Naturally, many such suspensions may be aerosolized subsequently and the a priori measurement of their number density in the carrier fluid will provide the basis for determining the subsequent airborne number densities following aerosolization.

BRIEF DESCRIPTION OF THE FIGURES

FIG. 1 shows the key elements of an absolute photometer that measures the light scattered into a detector from a small illuminated volume element.

FIG. 2 illustrates some key elements of a typical detector.

FIG. 3 shows elements of the detector and sample geometry used to calculate the excess Rayleigh ratio.

FIG. 4 represents the scattered intensity of 690 nm light at 90° from a mixture of 61 and 100 nm polystyrene spheres following separation by AsFFF.

FIG. 5 shows an enlargement of a region of FIG. 4 for which the absolute number densities will be calculated.

BRIEF DESCRIPTION OF THE INVENTION

In order to illustrate the inventive method, it is assumed that the particles of the suspension, whose absolute number density is sought, are homogeneous spheres. The method for determining the absolute number density of said suspended particles is comprised of a photometric procedure utilizing an absolute photometer capable of measuring directly the excess Rayleigh ratio from an illuminated sample. From such measurements, the suspended particles' mean diameter is determined. For monodisperse suspensions, a sample is prepared that has been diluted sufficiently to avoid multiple scattering that might degrade the scattering signals. The diluted sample is then placed into said absolute light scattering photometer where a fine light beam is made to pass through and illuminate a small region of said diluted sample. In the preferred embodiment of the invention, the light beam is polarized perpendicular to the scattering plane and provided by a laser operating at a single wavelength. The illuminated sample is surrounded by an array of well-collimated detectors, generally placed in said scattering plane containing also the incident light beam, each positioned to accept scattered light at a distinct angle with respect to the direction of the incident light beam. Assuming the particles are monodisperse, their refractive index relative to the refractive index of the liquid is used to calculate the mean particle size from the multiangle light scattering measurement made by said absolute light scattering photometer.

From the size calculated and the refractive index provided, the corresponding single particle differential scattered intensity is calculated from the Lorenz-Mie theory. The number density is then calculated immediately at any selected scattering angle by multiplying the measured excess Rayleigh ratio, $R(\theta)$, measured at said selected angle $\theta$, by $K^2$ and dividing by the corresponding Lorenz-Mie theory calculated differential scattered intensity value at the same scattering angle, where $k=2\pi n_0/\lambda_0$, $n_0$ is the refractive index of the suspending fluid, and $\lambda_0$ is the vacuum wavelength of the incident light. The excess Rayleigh ratio, of course, is the sum of the differential scattered intensities from all the particles present in the scattering volume.

If the particles are not monodisperse, yet spherical and of known refractive index, they must first be separated by means such as a cross flow field flow fractionator. Each such separated eluting fraction is then assumed to be monodisperse and its size and absolute number density is derived as described above.

For the more general case of arbitrarily shaped particles, such particles must be fractionated initially and an estimate of their size derived for each eluting fraction. From this and an estimate of the particles' mean refractive index, various models may be employed to calculate the differential scattered intensity value at a selected angle and derive the corresponding size and absolute number density as described above.

Although the ratio of the measured excess Rayleigh ratio, times $K^2$, divided by the calculated differential scattered intensity value at any selected angle will yield an absolute number density, the precision of this determination may be improved by calculating the number density at several scattering angles as described above and then averaging the results to obtain, thereby, a more precise result.

DETAILED DESCRIPTION OF THE INVENTION

The invention is most easily understood by reference to a monodisperse aqueous suspension of homogeneous spherical particles. Despite their simplicity, such samples are among the most common and important examples requiring the determination of the absolute particle number density. Examples of these samples include the familiar polystyrene latex, or PSL, spheres such as manufactured by the Duke Scientific Corporation of Palo Alto, Calif. and JSR Corporation of Tokyo, Japan. Such PSL samples are labeled with both their mean size and mass fraction. Generally, for particles whose diameters are below 1000 nm, the mass of PSL spheres per ml of solution is listed in %, i.e. % of 1 gm of PSL spheres per ml of solution. Thus the calculation of the actual number density present per ml of solution requires an a priori knowledge of the average particle size, the PSL mass density, viz. about 1.05, and the percent PSL in terms of gms PSL per ml liquid.

The aforementioned calculation is quite simple, yet the value derived depends critically upon accuracy of the three quantities provided. The relative fraction error in the calculated number density, $\Delta N/N$, is three times the relative fractional error of the particle size given. Thus a 2% error in the size presented will result in a 6% error in the number density calculated. Errors in the particle specific gravity provided also produce errors in the calculated number density, i.e. a 2% error in the specific gravity of the PSL particles will result in a 2% error in the absolute number density presented. Even the mass per ml number may contain some errors if evaporation has occurred or occurs with time. Adding to the possible errors, the sample polydispersity may not be accurately known.

By means of an absolute light scattering photometer, it becomes possible to determine the particle number density directly without knowledge of the particle's specific gravity relative to the suspending fluid. However, in order to calculate the particles' number density, one must be able to calculate the particles' differential scattered intensity which in turn requires an a priori knowledge of the particles' refractive index.

Figure 1:
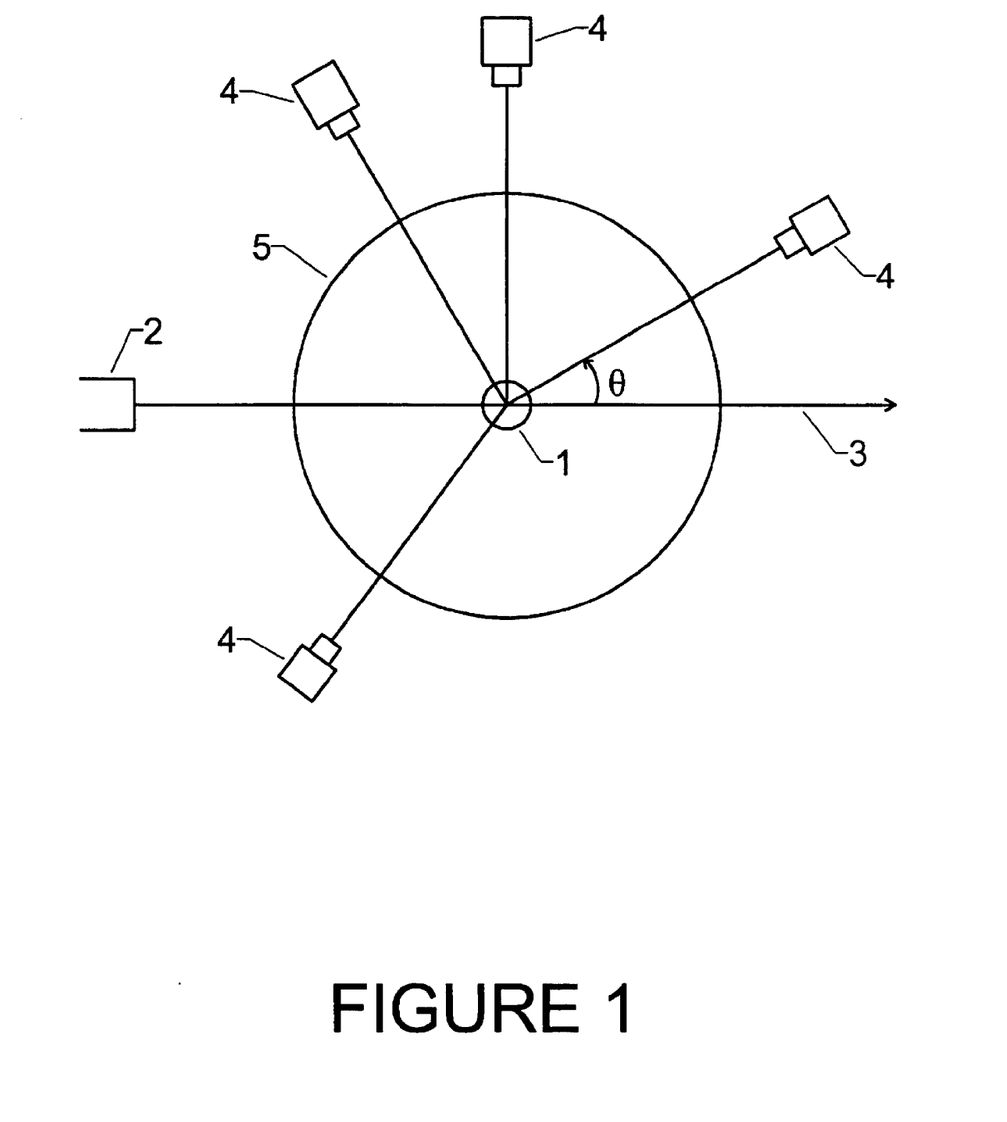
Figure 2:
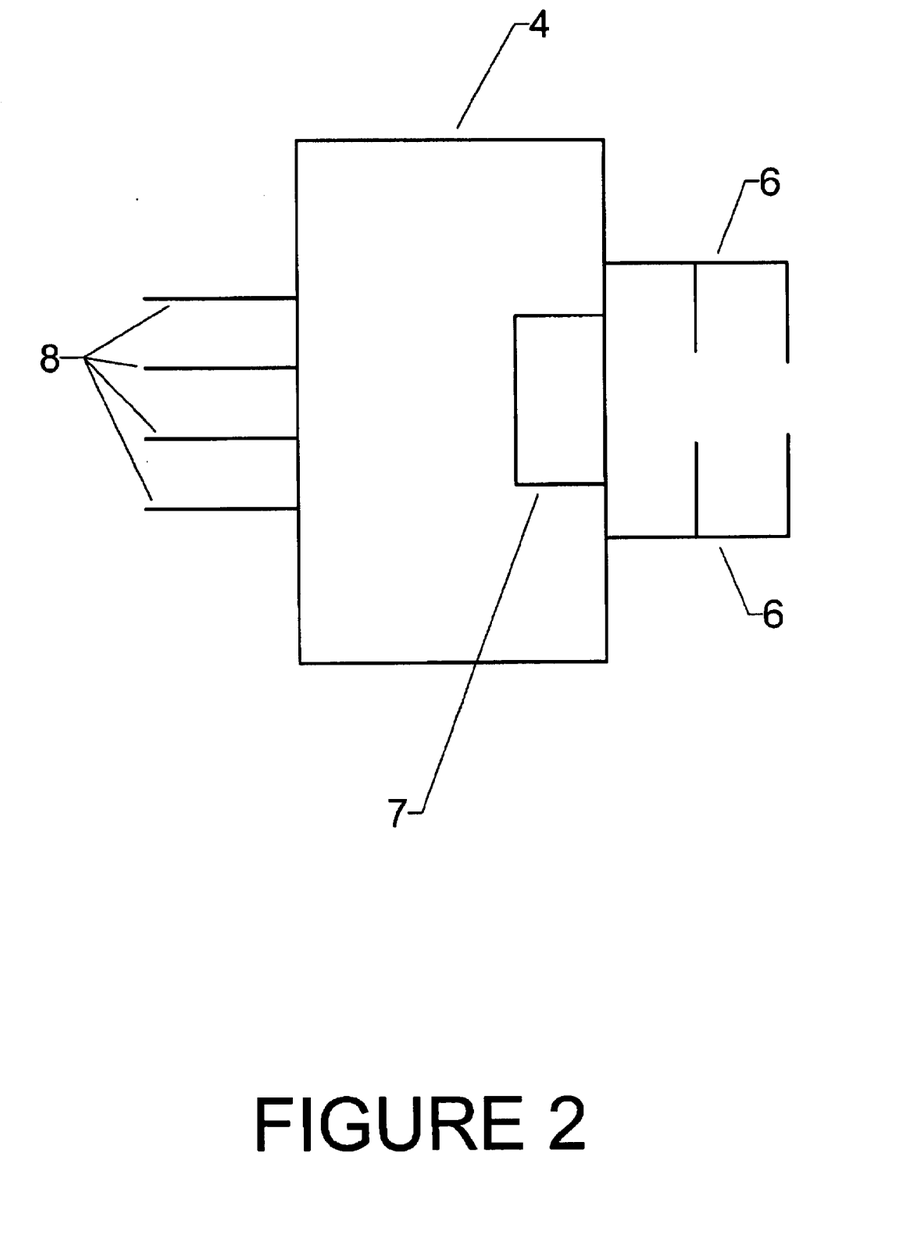

As shown schematically in FIG. 1, an absolute light scattering photometer is comprised of a sample holding cell 1, a light source 2 producing a fine beam of light 3, and an array of detectors 4 placed over a range of scattering angles θ. The preferred configuration of such an instrument provides for detectors confined in a plane along a circular path 5 with the sample being placed at the center of said path and the incident light beam lying along a diameter. The instrument is calibrated and normalized so that each detector measures the so-called Rayleigh ratio R(θ) at its corresponding angular location, θ, with respect to the direction of the incident light beam. FIG. 2 shows the key elements of a detector 4. This includes collimation means 6 and small detection area ΔA at 7 and electrical connections 8. The detectors themselves may be photodiodes, photomultipliers, various elements of photo diode arrays, as well as avalanche photodiodes and other light sensitive elements.

Figure 3:
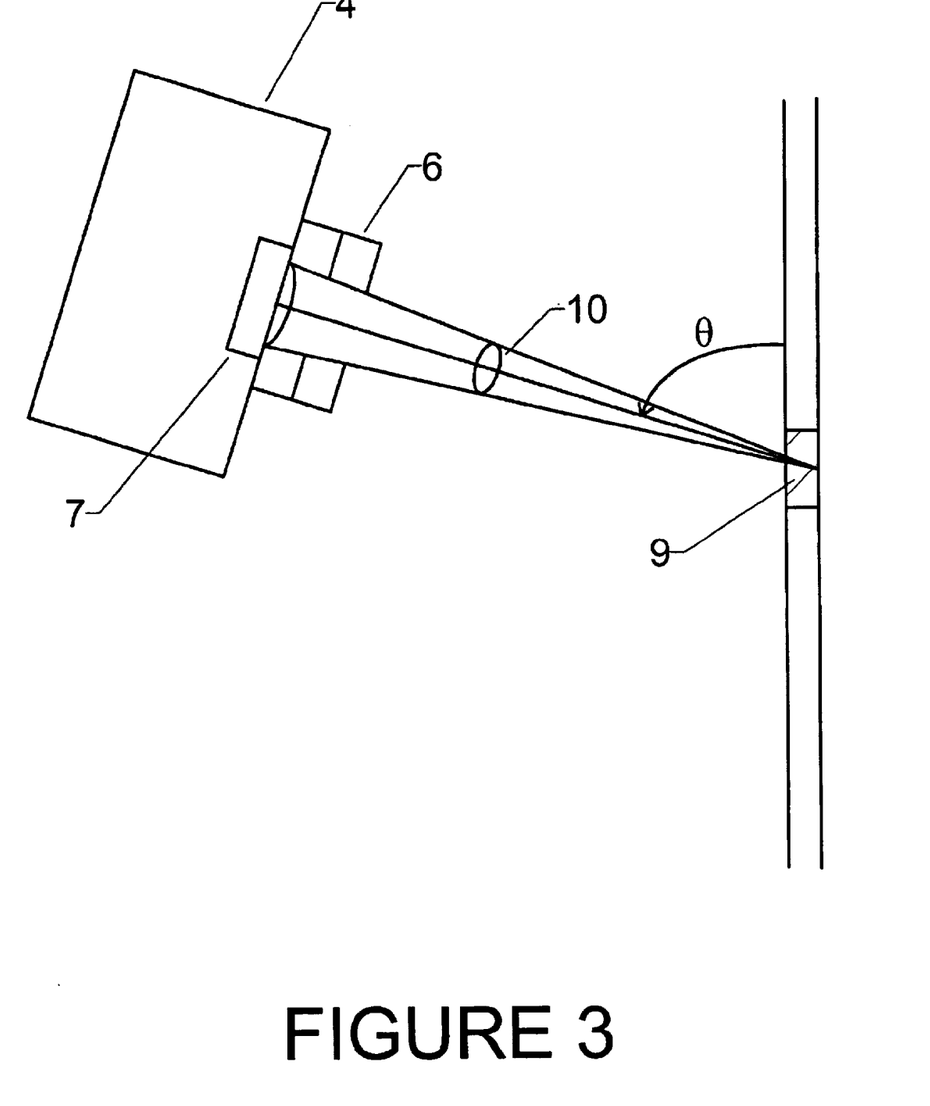

FIG. 3 shows key elements by which the Rayleigh ratio at scattering angle θ, R(θ), is determined. Only light scattered into the direction θ from the illuminated volume Δv at 9 and confined to the solid angle 10 reaches detector area 7. Solid angle 10, ΔΩ, is determined by the area at 7, ΔA, and the distance r from the scattering source 9, i.e. $\Delta\Omega = \Delta A/r^2$. The area, ΔA, seen at the scattered light source volume Δv 9 is defined by the collimating means shown at 6. The Rayleigh ratio, R(θ), is defined as the intensity of light falling into the solid angle ΔΩ from the scattering source at 9 onto the detector area 7 per unit volume per unit intensity of incident light, all in the limit as ΔΩ, ΔA, and Δv→0. The total volume 9, Δv, contributing to the measurement is determined from the detector's field of view which restricts the volume, Δv, of the illuminated sample whose scattered light may be intercepted by the detector. The determination of the suspended scattering particles' properties requires that the measured Rayleigh ratios be those in excess of any light scattered by the suspending fluid. Thus the measured Rayleigh ratios are corrected to subtract therefrom the corresponding scattering contributions of the suspending fluid. Thus, if the Rayleigh ratio of the solution at angle $\theta_i$ is $R_s(\theta)$ and the corresponding Rayleigh ratio of the suspending fluid is $R_f(\theta_i)$, then the excess Rayleigh ratio is defined as $R(\theta_i) = R_s(\theta_i) - R_f(\theta_i)$. Such excess Rayleigh ratios are required for all subsequent discussions herein.

It is shown, for example, in Kerker's book "The scattering of light," published by Academic Press of New York in 1969, that the intensity of scattered light from a single spherical particle, polarized in the direction described by the traditional polar angles θ and φ, is given by the expressions $$I_\varphi = \frac{I_0}{(kr)^2} i_1(\theta) \sin^2\varphi \quad (1)$$

$$I_\theta = \frac{I_0}{(kr)^2} i_2(\theta) \cos^2\varphi$$

where $k = 2\pi n_0/\lambda_0$, $\lambda_0$ is the wavelength of the incident radiation in vacuum, $I_0$ is the incident light intensity, r is the distance from the detector, and $n_0$ is the refractive index of the suspending medium. For measurements made in the θ plane with the incident light polarized perpendicular to the plane $$I_\varphi = I_1 = \frac{I_0}{(kr)^2} i_1(\theta)$$

where $i_1(\theta)$ is called the differential intensity or, simply, the single particle scattering function. Its complex dependence on the refractive index and radius of the scattering particles and the scattering angle θ is also given in Kerker's text as well as many other articles and optics texts. Similarly, the scattering function $i_2(\theta)$ is an equivalently complex function and describes the variation with θ for incident light polarized parallel to the scattering plane.

Consider now the detector 4 shown in FIG. 3 at the angle θ and a distance r from the small scattering volume Δv containing N identical particles per unit volume. The scattering intensity detected by the detector at angle θ for vertically polarized incident light would be just $$I_1 = \frac{I_0 N \Delta v}{(kr)^2} i_1(\theta) \quad (2)$$

Equation (2) may be expressed in terms of the Rayleigh ratio defined above as the intensity of light falling on the detector that had scattered into the solid angle about the direction θ from a unit volume illuminated by a unit intensity of incident light per steradian subtended by the detector, i.e.

$$\frac{I_1 r^2}{I_0 \Delta v} = R(\theta) = N i_1(\theta)/k^2. \quad (3)$$

Once the radius a and refractive index n of the identical particles in the illuminated volume Δv have been determined, one can use the Lorenz-Mie theory, such as described by Kerker, to calculate the corresponding single particle differential scattered intensity, $i_1(\theta)$. From a measurement of the excess Rayleigh ratio corresponding to the infinitesimal illuminated volume element Δv, the number of particles N per unit volume may be calculated immediately from $$N = \frac{k^2 R(\theta)}{i_1(\theta)}. \quad (4)$$

As discussed earlier, the number density determination of Eq. (4) may be calculated at any measured angle θ. By averaging over the entire range of angles collected during a MALS measurement, the precision of the determination may be improved. Since the precision and standard deviation of each excess Rayleigh ratio may be calculated as discussed by Shortt in his U.S. Pat. No. 5,528,366, a weighted average over all angles measured is easily achieved. The measurements required to determine the number densities of Eq. (4) are easily made by instruments such as the DAWN-EOS® light scattering photometers manufactured by Wyatt Technology Corporation of Santa Barbara, Calif. Calculations based on the Lorenz-Mie theory are readily performed by the associated ASTRA® software provided by the manufacturer. Numerous other sources of Lorenz-Mie software packages are easily found. The textbook "Absorption and scattering of light by small particles" by C. F. Bohren and D. R. Huffman published by John Wiley & Sons in New York in 1983 contains a variety of source code listings in FORTRAN for homogeneous and coated spheres. Although the total amount of light scattered depends upon the particle refractive index, the particle size generated from the measured variation with angle is far less dependent upon the particle refractive index. However, the most precise number density results will be obtained from precise refractive index values.

The simplest application of the technique thereto suggests, in the preferred embodiment of this invention, the choice of incident radiation as monochromatic with polarization perpendicular to the plane of measurement. Other polarizations of the incident light waves may be used as well, including unpolarized, circularly polarized, and elliptically polarized variations; however, the analytical interpretation of the data is most easily achieved for this preferred embodiment. The light beams used for these measurements are generated by lasers in the preferred embodiment of this invention, though other types of light sources such as Hg and Na discharge lamps with suitable collimating optics and wavelength filters may be suitable also for a variety of applications.

The determination of number densities for homogeneous, monodisperse spheres has been described above. But there are many other types of particles whose number densities must be determined also. Indeed, many such particles and their suspensions may have no a priori information available regarding their size or shape. For those whose shapes are known and regular, e.g. rods, disks, ellipsoids, etc., there are several means to approach the problem. In general, it is important to recognize the need to measure monodisperse distributions. Thus samples whose size ranges are not very narrow should be fractionated before such number density calculations are performed. For complex structures that may exhibit anisotropic composition, it may be necessary to place some detectors outside the conventional plane of measurement and/or fit polarization analyzers to some detectors to provide measurement of the elements of the so-called scattering matrix elements discussed, for example, by C. F. Bohren and D. R. Huffinan in their text cited above. These additional scattering properties provide additional information on which basis particle physical properties, such as anisotropic structure, may be more readily characterized.

If the particle structure is regular, appropriate measurements may be made to classify its average size using the complex analytical procedures developed initially by V. Erma in his 1968 papers appearing in the Physical Review, volume 173 pages 1243 to 1257 and volume 176 pages 1544 to 1553. Alternatively, one might assume that the particles are spherical and derive on a "best fit" basis average radius densities. Again, for such approximations, it is essential to make measurements of near homogeneous size distributions and to know a priori the mean refractive index of such particles. Another approach consists of assuming that the particles satisfy the conditions for application of the so-called Rayleigh-Gans-Debye, or RGD, approximation discussed in detail in the afore-referenced texts by Kerker and Bohren & Huffinan. In this event, one may derive the mean square radius, $<r_g^2>$, which is easily associated with the known structural parameters of the scattering particles. Thus for the case of homogeneous spheres of radius a, one has $$a^2 = \frac{3}{5} \langle r_g^2 \rangle.$$

Nevertheless, the refractive index is still needed to make the calculation of the type characterized by Eq.(4).

For particles whose refractive index is close to the refractive index of the suspending fluid, i.e. when m−1<<1 where m=n/n$_0$ and n is the refractive index of the particle, a simplified theory or approximation, the so-called Rayleigh-Gans-Debye, or simply RGD, approximation may be used. In this approximation, the dependence of the differential scattered intensity on the refractive index and size of the particle varies as $(m-1)^2 V^2$, and V is its volume. This dependence is seen for all particles for which the RGD approximation holds. For small, randomly oriented thin rods of radius a and length l, for example, one has $$i_1(\theta) = \frac{k^6 V^2 (m-1)^2}{2\pi^2} \left[ \frac{1}{z} Si(2z) - \left( \frac{\sin z}{z} \right)^2 \right] \quad (5)$$

where $V = \pi a^2 l$, $z = kl \sin(\theta/2)$, and $Si(x)$ is the sine integral of x. We could use the measured excess Rayleigh ratios to derive $<r_g^2>$ and determine the density distributions from the relation $$\langle r_g^2 \rangle = \frac{l^2}{12} \text{ for } l \gg a.$$

Similar approaches apply to other forms such as spheres, disks and ellipsoids. However, it should be noted that the differential scattered intensities depend directly on the refractive index of the scattering particles and their size. Subject to the validity criteria on which the RGD approximation is based, the range that these values realistically may have is very limited, and care must be exercised in interpreting light scattering signals from an ensemble of such particles.

Some particles may have a dielectric structure exhibiting spherical symmetry such as coated spheres or similar inhomogeneous structures. Calculation of the corresponding differential scattered intensity per particle, a function similar to the $i_1(\theta)$ of Eq. (4), is more complex and is described in detail in the paper by Wyatt appearing in volume 127 of the journal Physical Review, pages 1837 et seq. in 1962. Errata to this article were listed in volume 134, page AB1 in 1964.

We now return to the subject of polydisperse particle samples. As discussed earlier, in order to obtain a number fraction distribution, the sample must first be fractionated. Once fractionated, each eluting fraction, or slice, which is assumed monodisperse, is then analyzed to determine its particle density. From this the particle differential number fraction distribution is calculated. Referring to Eq.(4), we can write the number of particles $\Gamma_j$ present in slice j as $$\Gamma_j = N_j \Delta v_j = \frac{k^2 R_j(\theta)}{i_{1j}(\theta)} \Delta v_j, \quad (6)$$

where $R_j(\theta)$ is the excess Rayleigh ratio at that slice, and $\Delta v_j$ is the eluting fluid volume of that slice. Note that the differential scattered intensity must now be determined at each slice j as indicated by the added subscript j to $i_1(\theta)$. In other words, we must calculate the correct size corresponding to that of the assumed monodisperse particles in each slice. Once again, the number density, $N_j$ present in slice j may be calculated from measurements at any angle θ. More precisely, all angular determinations may be combined using a weighted average over the range of angles measured as discussed earlier. The total number of particles present in an injected volume $V_{inj}$, may be calculated directly by summing over the individual contributions of Eq. (6), assuming that the injected sample has been completely recovered following its separation. If each collection interval is the same, $\Delta v$, then the total number of particles $\Gamma$ of all fractionated sizes collected is $$\Gamma = \sum_j \Gamma_j = \sum_j N_j \Delta v_j = \sum_j \frac{k^2 R_j(\theta)}{i_1(\theta)} \Delta v_j = \Delta v \sum_j \frac{k^2 R_j(\theta)}{i_1(\theta)}. \quad (7)$$

The total particle number density of the injected sample is then just $$\Gamma / V_{inj} = \frac{\Delta v}{V_{inj}} \sum_j \frac{k^2 R_j(\theta)}{i_1(\theta)}. \quad (8)$$

Calculation of the differential number fraction at each slice is then straightforward from the ratios $\Gamma_j/\Gamma$.

Once a monodisperse sample has been confirmed, the inventive method is comprised of six steps:

1) Normalize and calibrate a light scattering photometer such that it measures, at a plurality of scattering angles, the Rayleigh ratio of the light scattered into the corresponding direction from the contributing illuminated volume;

2) Subtract from the measured Rayleigh ratios the Rayleigh ratios of the suspending fluid at the same scattering angles to derive the excess Rayleigh ratios;

3) Select a model to describe the scattering particles;

4) From the measured excess Rayleigh ratios at the plurality of scattering angles and the particle model selected, determine the effective size of the suspended particles;

5) From the derived size of the suspended particles, the model selected of the individual scattering particles, and the refractive index of the particle calculate the differential scattered intensity of a single particle at each of the scattering angles whose excess Rayleigh ratios have been measured; and 6) Multiply a selected excess Rayleigh ratio by $k^2$ and divide by the calculated differential scattered intensity at that same angle to deduce the number density of particles in the contributing illuminated volume.

In addition, as the excess Rayleigh ratios at all collected angular locations may be used to generate the same number density values, the individual contributions may be weighted, based on their calculated standard deviations, and averaged to yield an improved number density value together with its calculated standard deviation.

Figure 4:
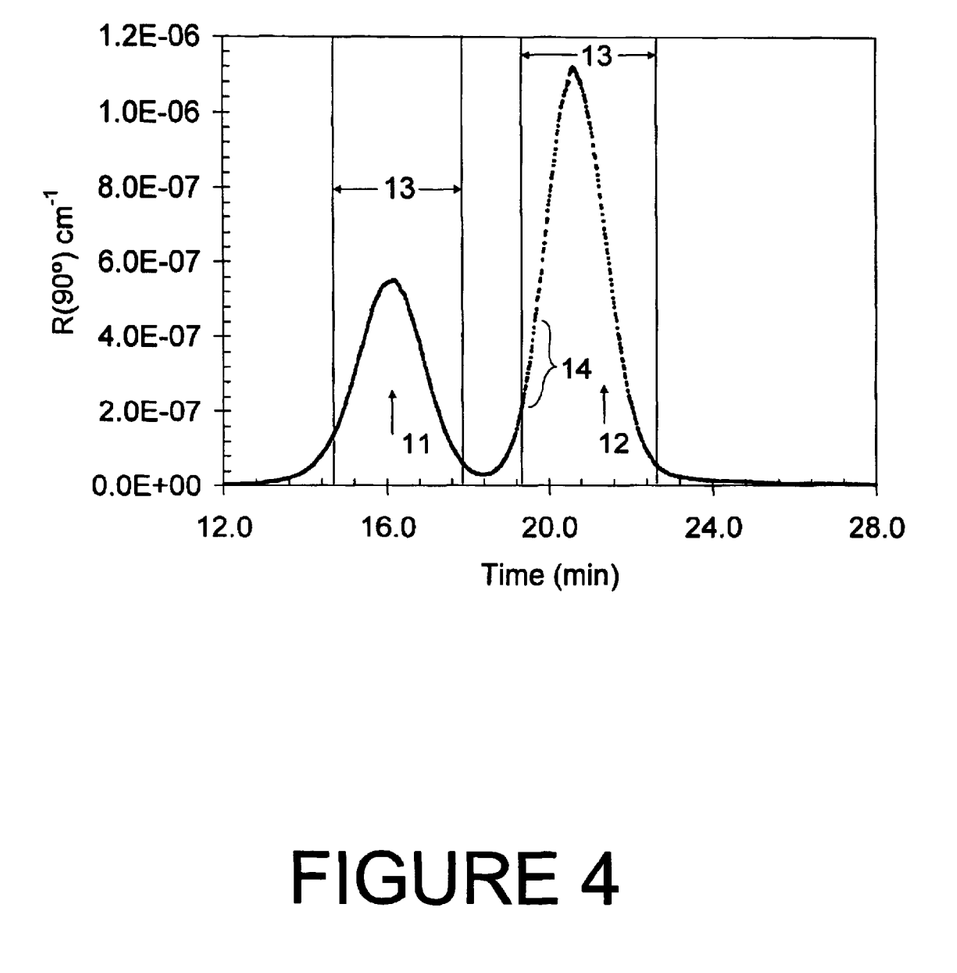

Consider now a sample comprised of 61 and 100 nm diameter polystyrene spheres separated by asymmetric field flow fractionation, or AsFFF. FIG. 4 shows the excess Rayleigh ratios at 90° in cm$^{-1}$ for the corresponding separated samples 11 and 12, respectively. The boundaries of the peaks selected are indicated by the horizontal lines 13. To illustrate the inventive method, consider a small region 14 of the nominal 100 nm peak shown in greater detail in FIG. 5. In Table 1, the measured excess Rayleigh ratios at 90° for the listed slices are shown together with their corresponding calculated geometrical radii. The radii were calculated using all of the excess Rayleigh

TABLE 1

Figure 5:
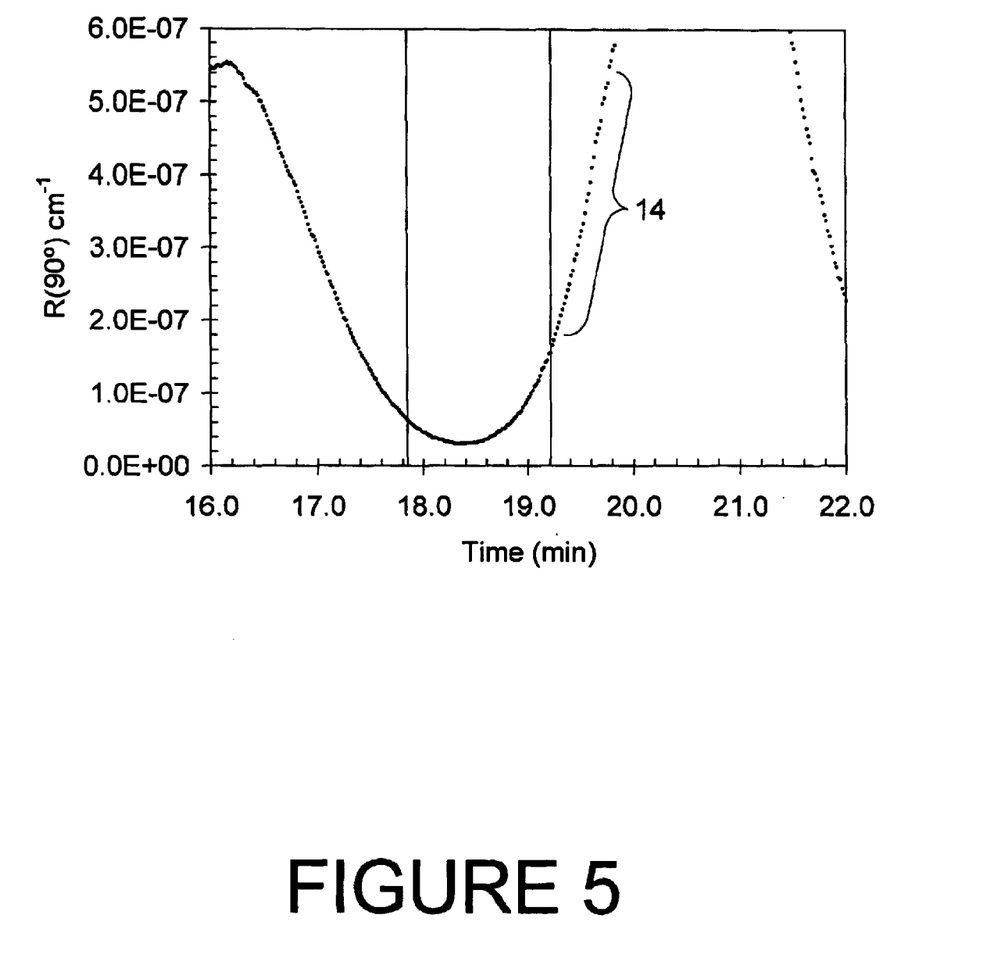

| | Region 14 of FIG. 5 | | | |
|---|---|---|---|---|
| Slice | $R(90°)$ cm$^{-1}$ | Radius (nm) | $i_1$ (90°) | $\Gamma$ |
| 211 | 1.55E − 07 | 47 | 4.580E − 04 | 8.248E + 04 |
| 212 | 1.55E − 07 | 47 | 4.580E − 04 | 8.300E + 04 |
| 213 | 1.66E − 07 | 47 | 4.580E − 04 | 8.878E + 04 |
| 214 | 1.73E − 07 | 48 | 5.180E − 04 | 8.175E + 04 |
| 215 | 1.81E − 07 | 48 | 5.180E − 04 | 8.547E + 04 |
| 216 | 1.89E − 07 | 47 | 4.580E − 04 | 1.009E + 05 |
| 217 | 1.97E − 07 | 47 | 4.580E − 04 | 1.051E + 05 |
| 218 | 2.07E − 07 | 49 | 5.840E − 04 | 8.652E + 04 |
| 219 | 2.16E − 07 | 47 | 4.580E − 04 | 1.150E + 05 |
| 220 | 2.23E − 07 | 48 | 5.180E − 04 | 1.054E + 05 |
| 221 | 2.32E − 07 | 48 | 5.180E − 04 | 1.096E + 05 | ratios at the 14 angles measured. The sample was fractionated using an asymmetric cross flow field flow fractionator, the "Eclipse," distributed by Wyatt Technology Corporation of Santa Barbara, Calif. The corresponding radius of the particles within each slice were then calculated assuming a particle refractive index of 1.58 using the Lorenz-Mie theory. From the calculated radii, the differential scattered intensity of a single particle, $i_1$ ($\theta$), at $\theta=90°$ was then calculated for each radius. Finally, following Eq. (4), the number of particles in each slice is calculated by dividing the excess Rayleigh ratio, $R(90°)$, by $\sigma(90°)$, multiplying by $k^2=[2*\pi*n_0/\lambda_0]^2=1.467*10^{10}$ cm$^{-2}$, and multiplying by the slice volume $\frac{1}{60}$ ml. The results by slice are shown in the last column.

The total number of eluting particles contributing to the peak of the separated particles may be calculated by summing over all contributing slices. The differential number fraction at each slice is then the ratio of the number of particles in that slice divided by the total number of eluting particles. As each slice corresponds to a specific size, within some calculable range, the differential results from all the slices may be combined to permit calculation of the cumulative fraction distribution, as well. If the volume of the injected aliquot is known, as it usually is, then the differential number density distribution of the source is readily found. Thus the total particle density of the injected source is obtained by dividing the total number of particles calculated by the surmising procedure discussed above by the volume of the injected source. Similarly, the number density of a particular type of eluting particle, perhaps corresponding to those eluting in a separate peak, may be obtained by summing the number of such particle measured in the eluting sample and diving the sum by the volume of the injected sample. There are many other types of analyses that may be performed once such differential number fractions and densities have been calculated over the range of eluting samples. All of these are but obvious extensions of the examples presented here.

It is important to point out that if the number of particles injected into a separation device, such as the AsFFF fractionator discussed earlier, is known and no particles are retained within the separation mechanism itself, this same number must correspond to the total number calculated by adding up all the derived numbers within all the slices recovered in the separation. Generally, such separations are associated with a dilution of the injected volume into the greater volume occupied by the total contributing volume, i.e. the sum over all slice volumes. Conversely, given the injection volume and the volume recovered following fractionation and summing over all eluting fractions, the number density of the injected volume must correspond to the total number of particles recovered divided by the injected volume. In addition, for any specific size group of particles recovered following fractionation, the number density of that size group in the injected volume is just the ratio of the number in the selected size group divided by the injected volume. On this basis, the differential number density associated with any fractionated sample may be calculated.

As will be evident to those skilled in the art of light scattering from small particles, there are many possible variations and implementations of the described method all of which will at this time be obvious. Light sources may be lasers producing light at various wavelengths and polarizations, collimated conventional light sources emitting light at single or multiple wavelengths, as well as light emitting diodes. Sample cells may be of extremely small size such as would be found in instrumentation designed to measure nanogram quantities or large cells such as scintillation vials used to hold samples of several milliliters in volume. As mentioned earlier, detectors, though generally collimated, may be of various kinds. The methods disclosed here have broad applicability using any of these implementations.

We claim:

1. A method for determining the number density of monodisperse particles in solution comprising the steps of
   A) Normalizing and calibrating a light scattering photometer, incorporating a fine beam of monochromatic light operating at a wavelength $\lambda_0$, to produce measurements at a plurality of scattering angles $\theta_i$, of the corresponding Rayleigh ratios $R^s$ ($\theta_i$) of the light scattered into the corresponding direction $\theta_i$ from a contributing illuminated volume;
   B) Introducing a particle-containing solution into said normalized and calibrated photometer;
   C) Measuring the Rayleigh ratios $R^s$ ($\theta_i$) of said particle-containing solution;
   D) Subtracting from said measured Rayleigh ratios, $R^s$ ($\theta^i$), the corresponding Rayleigh ratios $R^f$ ($\theta_i$) of the suspending fluid at the same scattering angles $\theta_i$ to derive the excess Rayleigh ratios $R(\theta_i)=R^s$ ($\theta_i$)$-R^f$ ($\theta_i$)at each said scattering angle $\theta_i$;
   E) Selecting a model to describe the scattering particles;
   F) Deriving the effective size of said monodisperse particles in said particle-containing solution from said measured excess Rayleigh ratios at said plurality of scattering angles based on said particle model selected;
   G) Calculating the differential scattered intensity i($\theta_i$)of a single particle at each of said scattering angles from said derived effective size of said suspended monodisperse particles, the model selected of the individual scattering particles, and the refractive index of each said particle; and
   H) Calculating the number density N of said monodisperse particles in said contributing illuminated volume by multiplying a selected excess Rayleigh ratio at one measured angle $\theta_i$ by $k^2=(2\pi n_0/\lambda_0)^2$ and dividing said product by said calculated differential scattered intensity corresponding to said same angle to yield $N=R(\theta_i)k^2/i(\theta_i)$, where $n_0$ is the refractive index of the solution and $\lambda_0$ is the vacuum wavelength of the incident light.

2. The method of claim 1 where said monochromatic fine beam of light is from a laser.

3. The method of claim 1 where said absolute number density value is calculated using an excess Rayleigh ratio measured at a different scattering angle than that chosen in said claim 1 and using corresponding calculated differential scattered intensity, said different absolute number density then averaged with earlier calculated absolute number density.

4. The method of claim 3 where data at additional scattering angles are used to calculate additional absolute average number densities therefrom.

5. The method of claim 1 where said monochromatic incident fine beam of light is plane polarized.

6. The method of claim 5 where said plane polarized beam of light is vertically polarized with respect to the scattering plane containing said scattered light detectors.

7. The method of claim 1 where said monodisperse particles are homogeneous spheres.

8. The method of claim 7 where said differential scattered intensities $i(\theta_i)$ of a single particle are calculated from Lorenz-Mie theory.

9. The method of claim 1 where said model is the Lorenz-Mie theory.

10. The method of claim 1 where said model is a spherical model based on the Rayleigh-Gans-Debye approximation.

11. The method of claim 1 where said model is based on the formulation of Erma.

12. The method of claim 1 where said model is based on the formulation of Wyatt.

13. The method of claim 1 where said monochromatic incident fine beam of light is unpolarized.

14. The method of claim 1 where said monochromatic incident fine beam of light is circularly polarized.

15. A method for determining the differential number fraction distribution for a suspension of polydisperse particles comprising the steps of A) Injecting an aliquot of said particle suspension into a separation means, said means separating said particles based on their size;

B) Measuring the Rayleigh ratio $R^f(\theta_i)$ at a set of scattering angles $\theta_i$ of the fluid suspending said particles;

C) Measuring the Rayleigh ratio $R^s(\theta_i)$ at a set of scattering angles $\theta_i$ of each eluting fraction of such separated particles by passing them through an absolute light scattering photometer means, each said eluting fraction corresponding to a monodisperse size fraction of said original suspension of particles;

D) Determining the excess Rayleigh ratios $R(\theta_i) = R^s(\theta_i) - R^f(\theta_i)$ at each said scattering angle $\theta_i$, for each said eluting fraction;

E) Selecting a model to describe the scattering particles of each said eluting fraction;

F) Deriving the effective size of said eluting monodisperse particles in said eluting fraction from said measured excess Rayleigh ratios at said plurality of scattering angles using said particle model selected;

G) Calculating the differential scattered intensity $i(\theta_i)$ of a single particle at each selected scattering angle $\theta_i$ from said derived effective size of said suspended monodisperse particles, the model selected of the individual scattering particles, and the refractive index of each said particle; and H) Calculating the number density N of said monodisperse particles in said contributing illuminated volume by multiplying said selected excess Rayleigh ratio at said selected angle $\theta_i$ by $k^2 = (2\pi n_0/\lambda_0)^2$ and dividing said product by said calculated differential scattered intensity $i(\theta_i)$ corresponding to said same angle to yield $N = R(\theta_i)k^2/i(\theta)$;

I) Multiplying said number density of particles in each said eluting volume by the corresponding volume of each said eluting volume to obtain number of particles in said eluting volume; and J) Summing the total number of particles so-determined in a range of eluting fractions to obtain the total number of particles injected into said separation means; and K) Dividing said number of particles of said eluting by said total number of particles injected to obtain the differential number fraction for said eluting fraction.

16. The method of claim 15 where said absolute light scattering photometer provides means to illuminate said separated particles with a monochromatic fine beam of light.

17. The method of claim 16 where said monochromatic fine beam of light is from a laser.

18. The method of claim 15 where each said absolute number density value is calculated using an excess Rayleigh ratio measured at a different scattering angle than that chosen in said claim 15 and using corresponding calculated differential scattered intensity, each said different absolute number density then averaged with earlier calculated absolute number density.

19. The method of claim 18 where data at additional scattering angles are used to calculate additional absolute average number densities therefrom.

20. The method of claim 15 where said monochromatic incident fine beam of light is plane polarized.

21. The method of claim 15 where said monochromatic incident fine beam of light is unpolarized.

22. The method of claim 15 where said monochromatic incident fine beam of light is circularly polarized.

23. The method of claim 20 where said plane polarized beam of light is vertically polarized with respect to the scattering plane containing said scattered light detectors.

24. The method of claim 15 where said monodisperse particles are homogeneous spheres.

25. The method of claim 15 where said differential scattered intensities $i(\theta_i)$ of a single particle are calculated from Lorenz-Mie theory.

26. The method of claim 15 where said model is the Lorenz-Mie theory.

27. The method of claim 15 where said model is a spherical model based on the Rayleigh-Gans-Debye approximation.

28. The method of claim 15 where said model is based on the formulation of Erma.

29. The method of claim 15 where said model is based on the formulation of Wyatt.

* * * * *

UNITED STATES PATENT AND TRADEMARK OFFICE
CERTIFICATE OF CORRECTION

PATENT NO. : 6,774,994 B1  
APPLICATION NO. : 10/640893  
DATED : August 10, 2004  
INVENTOR(S) : Philip J. Wyatt and Miles J. Weida Page 1 of 1

It is certified that error appears in the above-identified patent and that said Letters Patent is hereby corrected as shown below:

Column 6, Line 54 reads, " $a^2 = \frac{3}{5}\langle r_g^2 \rangle.$ " and should read " $\langle r_g^2 \rangle = \frac{3}{5}a^2.$ "

Column 9, Line 29 is improperly formatted to read, "k²=[2*π*$n_0$/$\lambda_0$]$^{2=1.467*1010'}$ cm-2, and multiplying by the" and should read "$k^2$=[2*π*$n_0$/$\lambda_0$]$^2$ = 1.467*10$^{10}$ cm$^{-2}$, and multiplying by the"

Signed and Sealed this

Seventh Day of April, 2009

JOHN DOLL  
*Acting Director of the United States Patent and Trademark Office*